US009526586B2

(12) United States Patent
Wade (10) Patent No.: US 9,526,586 B2
(45) Date of Patent: Dec. 27, 2016

(54) SOFTWARE TOOLS PLATFORM FOR MEDICAL ENVIRONMENTS

(71) Applicant: Z Microsystems, Inc., San Diego, CA (US)

(72) Inventor: Jack Wade, La Jolla, CA (US)

(*) Notice: Subject to any disclaimer, the term of this patent is extended or adjusted under 35 U.S.C. 154(b) by 171 days.

(21) Appl. No.: 14/107,329

(22) Filed: Dec. 16, 2013

(65) Prior Publication Data

US 2015/0046818 A1     Feb. 12, 2015

Related U.S. Application Data

(60) Provisional application No. 61/865,037, filed on Aug. 12, 2013.

(51) Int. Cl.
| | | |
|---|---|---|
| *G06F 3/048* | (2013.01) | |
| *A61B 19/00* | (2006.01) | |
| *A61B 1/313* | (2006.01) | |
| *A61B 1/00* | (2006.01) | |

(52) U.S. Cl.
CPC .............. *A61B 19/56* (2013.01); *A61B 34/25* (2016.02); *A61B 1/00009* (2013.01); *A61B 1/3132* (2013.01); *A61B 90/361* (2016.02); *G06T 2200/24* (2013.01); *G06T 2207/30004* (2013.01)

(58) Field of Classification Search
CPC ..... G09G 3/20; G06F 19/3418; G06F 19/3481
See application file for complete search history.

(56) References Cited

U.S. PATENT DOCUMENTS

| | | | | |
|---|---|---|---|---|
| 2003/0159141 A1* | 8/2003 | Zacharias | ............... | A61B 19/52 725/37 |
| 2006/0125935 A1* | 6/2006 | Torvinen | .................. | H04N 1/00 348/231.99 |
| 2008/0316304 A1* | 12/2008 | Claus | .................. | G06F 19/3406 348/61 |
| 2010/0020917 A1* | 1/2010 | Gagliano | ............. | A61B 5/0002 378/4 |
| 2012/0075968 A1* | 3/2012 | Watanabe | ............ | G11B 27/034 369/30.08 |
| 2012/0226150 A1* | 9/2012 | Balicki | ................ | A61B 5/0066 600/424 |
| 2015/0140535 A1* | 5/2015 | Geri | ........................ | G09B 23/28 434/262 |

\* cited by examiner

*Primary Examiner* — William Bashore
*Assistant Examiner* — Rayeez Chowdhury
(74) *Attorney, Agent, or Firm* — Olivo Law Group, P.C.; John W. Olivo, Jr.

(57) ABSTRACT

Various embodiments provide a medical software tools platform that utilizes a surgical display to provide access to medical software tools, such as medically-oriented applications or widgets, that can assist those in the operating room, such as a surgeon and their surgical team, with a surgery. For various embodiments, the medical software tools platform and its associated medical software tools are presented on a surgical display (e.g., being utilized in an operating room) over an image stream provided by a surgical camera (e.g., in use in the operating room). Various medical software tools can provide features and functions that can facilitate integration of equipment in an operating room or add medical context awareness to anatomic structures presented in the image stream from the surgical camera.

25 Claims, 6 Drawing Sheets

Medical Software Tools Platform System 300

- Image Stream Interface Module
  302
- User Interface Overlay Module
  304

Medical Software Tools 306

| Medical Device Control Module 312 | Image Similarity Search Module 314 |
|---|---|
| Image Stream Processing Control Module 316 | Measurement Module 318 |
| Image Stream Tagging and Tracking Module 320 | Stereoscopic Image Stream Module 322 |
| Image Logging Module 324 | Timer Module 326 |
| Image Enhancement Module 328 | Embedded-Object Tracking Module 330 |

Checklist Module
332

Medical Device Interface Module
308

Image Stream Processing System Interface Module
310

SOFTWARE TOOLS PLATFORM FOR MEDICAL ENVIRONMENTS

CROSS-REFERENCE TO RELATED APPLICATIONS

This application claims the benefit of U.S. Provisional Patent Application Ser. No. 61/865,037, filed Aug. 12, 2013, entitled "TOOLS PLATFORM FOR MEDICAL ENVIRONMENTS," which is hereby incorporated herein by reference.

TECHNICAL FIELD

The technology disclosed herein relates to medical software tools and, in particular, some embodiments provide systems and methods relating to a software tools platform for a medical environment, such as a surgical environment.

DESCRIPTION OF RELATED ART

Minimally invasive surgeries increasingly occur in operating rooms equipped with advanced audio visual technology. At one end of the spectrum are integrated operating rooms, that combine high resolution video displays, touchscreen control, access to digital information through the hospital network, and data archiving capability into an interconnected purpose-built system. In addition to facilitating surgical procedures and improving efficiency, integrated operating rooms can also connect the surgeon in the sterile field with people and information outside the operating room. For example, an integrated operating rooms can enable: live consultation with pathology and ICU; real-time collaboration with surgeons across the globe; live feeds to conference rooms and auditoriums for training and grand rounds; and data exchange with an electronic medical record system, radiological picture archiving and communication system (PACS), or network-enabled devices in other operating and treatment rooms.

BRIEF SUMMARY OF EMBODIMENTS

Various embodiments of the disclosed technology provide a medical software tools platform that utilizes a surgical display to provide access to medical software tools, such as medically-oriented applications or widgets, that can assist those in the operating room, such as a surgeon and their surgical team, with a surgery. For various embodiments, the medical software tools platform and its associated medical software tools are presented on a surgical display (e.g., being utilized in an operating room) over an image stream provided by a surgical camera (e.g., in use in the operating room) or other medical device that generates image streams. An image stream can include video or a series of static images (e.g., medical ultrasound device). Various medical software tools can provide features and functions that can facilitate integration of equipment in an operating room or add medical context awareness to anatomic structures presented in the image stream from the surgical camera.

According to some embodiments, a system comprises an image stream interface module configured to receive an image stream from a surgical camera, a user interface overlay module configured to provide a user interface overlay adapted for presentation over the image stream, and a medical software tools module configured to provide a medical software tool through the user interface overlay. The medical software tool may be configured to perform an operation with respect to the image stream and provide an output adapted to be presented over the image stream. The user interface overlay can include a graphical user interface (GUI) that permits visibility of at least some of the image stream underlying the user interface overlay. The user interface overlay module is further configured to present the output over the image stream. Depending on the embodiment, the surgical camera may be an endoscope or a laparoscope. Additionally, the image stream interface module may receive the image stream from the surgical camera through an image stream processing system.

Throughout this description, a user interface will be understood to be accessible to any user involved in a medical procedure, such as a surgery. It will also be understood that a user can include any individual involved in a given medical procedure, such as a nurse or a surgeon.

In some embodiments, the system comprises a medical device communication module configured to exchange data between a medical device and the medical software tool. Through the medical device interface module, some embodiments can enable a medical software tool to present information from disparate medical devices, or facilitate sharing of information between medical devices. In some embodiments, the system comprises an image stream processing system interface module configured to exchange data between an image stream processing system and the medical software tool, the medical software tool being configured to modify a setting of the image stream processing system. The setting of the image stream processing system can include enabling or disabling application of an image stream processing algorithm to the image stream. Through the image stream processing system interface module, the medical software tool can control how the image stream processing system receives and processes image streams eventually presented on the surgical display.

Depending on the embodiment, the operation performed by the medical software tool may comprise a visual tag over the image stream in association with an anatomical structure or tissue presented in the image stream, and the output may comprise the visual tag. A timer may be associated with respect to the visual tag. The operation performed by the medical software tool may comprise measuring an anatomical structure or tissue (e.g., width, height, length, or volume) presented in the image stream, and the output may comprise a resulting measurement. Where the image stream comprises two-dimensional content, the operation may comprise converting at least some of the two-dimensional content into three-dimensional content, and the output may comprise the three-dimensional content (e.g., stereoscopic three-dimensional content). The operation performed by the medical software tool may comprise associating content in the image stream with a timer, and the output may comprise a visual representation of the timer. The operation performed by the medical software tool may comprise identifying content (e.g., anatomic structure) in the image stream similar to reference content (e.g., reference anatomic structure), and the output may comprise a visual indication of the identified content.

According to some embodiments, a computer program product comprises code configured to cause a computer system to perform various operations described herein. Additionally, some embodiments may be implemented using a computer system as described herein.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit inventions described herein to the precise form disclosed. It should be understood that any invention described herein can be practiced with modification and alteration, and that the disclosed technology be limited only by the claims and the equivalents thereof.

DESCRIPTION OF EMBODIMENTS OF THE TECHNOLOGY

Various embodiments provide systems and methods that relate to medical software tools platforms. According to some embodiments, a medical software tools platform can utilize a surgical display, such as one utilized during a laparoscopic or endoscopic surgery, to facilitate an integrated operating room. According to some embodiments, the medical software tools platform can leverage the surgical display to provide access to medical software tools, such as medically-oriented applications or widgets, that can assist those in the operating room (e.g., the surgeon and their surgical team) with a surgery. For various embodiments, the medical software tools platform and its associated medical software tools are presented on a surgical display (e.g., being utilized in an operating room) over an image stream provided by a surgical camera (e.g., in use in the operating room) or other medical device that generates image streams. It will be understood that an image stream can include video or a series of static images (e.g., medical ultrasound device).

Features and functions provided by the medical software tools can include, without limitation, centrally gathering information from disparate operating room equipment (e.g., equipment from different medical vendors), and presenting the information on a surgical display or sharing the information between operating room equipment. In this way, the surgical display may function as an information hub in an operating room while avoiding the risk of defocusing a surgeon's attention with multiple medical device screens in the operating room. Features and functions provided by the medical software tools can include, without limitation, interactive augmentation of image streams presented on a surgical display, such as tagging and tracking of anatomic structures presented in an image stream being presented on the surgical display. Features and functions provided by the medical software tools may further include, without limitation, on-screen analysis of anatomical structures or tissue presented in an image stream. Features and functions provided by the medical software tools can include, without limitation, control a function or setting of a piece of medical equipment being used in an operating room. In some embodiments, a medical software tool controls a function or setting of an image stream processing system applying one or more algorithms to an image stream being presented on a surgical display. Features and functions provided by the medical software tools can include, without limitation, augmenting an image stream presented on a surgical display with medical context awareness. For instance, a medical software tool may identify anatomical structures or tissue presented in the image stream, search for anatomic similarities presented in the image stream, or allow for a "sticky" annotation (e.g., tag or comment) to be associated with an anatomic structure presented in the image stream such that the positioning of the annotation tracks movement of the anatomic structure (e.g., as the surgical camera is repositioned or anatomic structure shift position). Features and functions provided by the medical software tools can include, without limitation, providing access to patient medical records (e.g., text or imagery), possibly from hospital internal network. Features and functions provided by the medical software tools can include, without limitation, management of one or more windows over the image stream that facilitate various image-based functions, such as application of image algorithms or sharing contents within the window with remote peers.

Depending on the embodiment, medical software tools can be flexibly added or removed from the medical software tools platform based on user-preferences (e.g., surgeon preferences) or as needed. Additionally, the availability of medical software tools through the platform may adapt according to the context currently selected or detected with respect to content being presented in the image stream. For example, upon detecting certain anatomic structures being presented in the image stream, such as blood vessels or certain organs, the medical software tools platform may present the availability of one or more medical software tools known to be useful when operating on or around the blood vessels or the certain organs. The availability of medical software tools through the platform may also be determined through user preferences (e.g., surgeon preferences), which may be learned by the platform through past use of medical software tools in connection with certain contexts.

As a surgical display can provide those in an operating room (e.g., a surgeon and their surgical team) with a live view of a patient's surgery, various embodiments can utilize the surgical display to provide access to a platform having one or more medical software tools that can be useful during an operation. Though various embodiments described herein are done so with respect to surgical displays or the like, those skilled in the art will appreciate that some embodiments can employ other types of displays used in medical environments. Additionally, though various embodiments described herein are done so with respect to surgical displays, those skilled in the art will appreciate that some embodiments can involve static images provided by a surgical camera.

Figure 1:
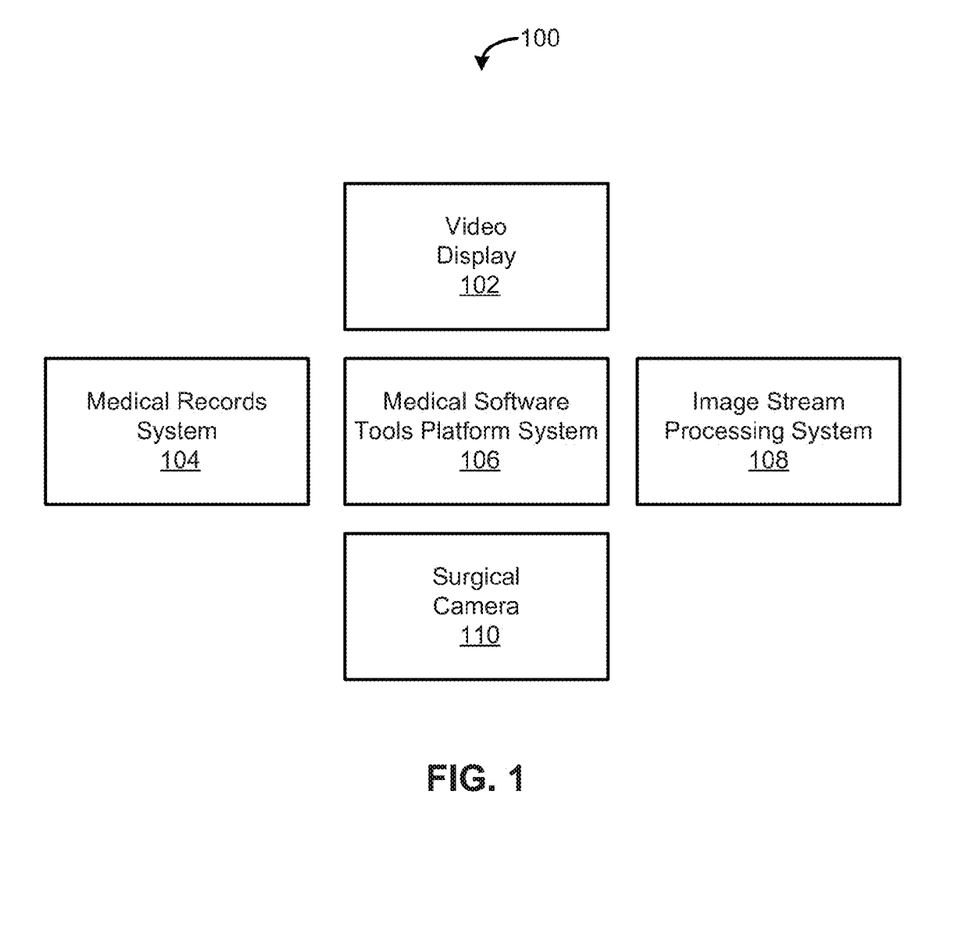
FIG. 1 is a block diagram illustrating an example environment in which a medical software tools platform system is implemented in accordance with some embodiments of the technology described herein.

FIG. 1 is a block diagram illustrating an example environment 100 in which a medical software tools platform system 106 is implemented in accordance with some embodiments of the technology described herein. The example environment 100 may be one found in an operating room, where by the medical software tools platform system 106 provides a surgeon or their surgical team with access to medical software tools that can assist during surgical procedures performed in the operating room. As shown, the example environment 100 includes a video display 102, a medical records system 104, the medical software tools platform system 106, an image stream processing system 108, and a surgical camera 110. For some embodiments, the medical software tools platform system 106 is communicatively coupled to one or more of the video display 102, the medical records system 104, the image stream processing system 108, and the surgical camera 110. Depending on the embodiment, the medical software tools platform system 106 may communicate with one or more of the video display 102, the medical records system 104, the image stream processing system 108, and the surgical camera 110 using various types of communication interfaces, including wired or wireless network communications (e.g., Ethernet) or wire or wireless serial communications (e.g., USB, IEEE 1394, Bluetooth, etc.). Depending on the embodiment, a user (e.g., surgeon) may interact with the medical software tools platform system 106 through a human interface device, such as a mount or keyboard. In some embodiments, the video display 102 is touch-enabled and facilitates user interactivity between a user and the medical software tools platform system 106. Additionally, in some embodiments, the medical software tools platform system 106 is configured to receive user input as voice commands, which may be facilitated through a medical software tool included by the medical software tools platform system 106.

The medical software tools platform system 106 may provide a user interface overlay adapted for presentation over an image stream being presented on the video display 102, and provide a medical software tool through the user interface overlay. The image stream presented by the video display 102 may be one originating from the surgical camera 110. Accordingly, the content of the image stream may show anatomical structures or tissue typically encountered during surgery, including internal organs and tissue of a patient being operated upon. The medical software tool may be one of several offered by the medical software tools platform system 106, and may perform an operation with respect to the image stream from the surgical camera 110. The operation performed by a medical software tool of the medical software tools platform system 106 can include, without limitation, image stream enhancement, management of windows for window-based functions, timers (e.g., clocks, countdown timers, and time-based alarms), tagging and tag tracking, image stream logging, performing measurements, two-dimensional to three-dimensional content conversion, and similarity searches. The medical software tools platform system 106 may provide output resulting from the operation for presentation over the image stream. As described herein, the user interface overlay may include a graphical user interface (GUI) that permits visibility of at least some of the image stream underlying the user interface overlay. For some embodiments, the medical software tools platform system 106 may be integrated, in whole or in part, into the video display 102 or the image stream processing system 108.

The video display 102 may be one commonly utilized in medical environments during medical procedures, such as a surgical display common to endoscopic camera systems, laparoscopic camera systems, and the like. For some embodiments, the video display 102 is a touch screen display that facilitates user interactivity between a user (e.g., surgeon) and the medical software tools platform system 106. For various embodiments, the video display 102 is coupled to the medical software tools platform system 106 and the image stream presented on the video display 102 is routed through the medical software tools platform system 106. As the image stream is routed through the medical software tools platform system 106 to the video display 102, the system 106 may overlay a user interface to the medical software tools platform, and its associated medical software tools, over the image stream. Alternatively, in some embodiments, the video display 102 is coupled to the image stream processing system 108 and the image stream presented on the video display 102 is routed through the image stream processing system 108. As the image stream is routed through the image stream processing system 108 to the video display 102, the system 108 may receive a user interface to the medical software tools platform, and its associated medical software tools, from the medical software tools platform system 106 and overlay the user interface over the image stream. As described herein, the user interface may be overlain over the image stream such that visibility to at least some of the image stream underlying the user interface is maintained. Those skilled in the art will appreciate that various embodiments can include alternative configurations to those described herein.

The medical records system 104 may provide access to patient medical records, possibly from a private hospital network. The content of the patient medical records may comprise a variety of formats, including images, audio, video, and text (e.g., document). For some embodiments, a medical software tool of the medical software tools platform system 106 may access information from a patient medical record and provide such information through the user interface presented over the image stream on the video display 102. Depending on the embodiment, the medical software tool may extract the information from the patient medical record and augment the image stream with the extracted information, analyze the extracted information and augment the image stream in response, or both. For instance, a medical software tool of the medical software tools platform system 106 may select an x-ray image from a patient's medical record and overlay the selected image over the image stream, which may guide a surgeon in performing certain steps of a surgical procedure.

The image stream processing system 108 may receive one or more live image streams from one or more image stream sources (e.g., medical devices in an operating room, such as an endoscope), and applies one or more image stream processing algorithms to the received image streams. For some embodiments, the image stream processing system 108 can simultaneously receive and switch between multiple input image streams to multiple output devices while providing image stream processing functions on the image streams. The incoming image streams may come from various medical devices including, without limitation, surgical cameras and medical ultrasound devices. The image streams received by the image stream processing system 108 may vary in resolution, frame rate, format, and protocol according to the characteristics and purpose of their respective source device. The image stream processing system 108 can be iteratively route through a reconfigurable array of image processing circuits to operate on one or more streams using preprogrammed algorithms. Depending on the embodiment, the image stream processing system 108 can route resulting image streams through another processing function, or to an output circuit that sends the processed image stream for presentation on the video display 102, to a recording system, across a network, or to another logical destination.

In the image stream processing system 108, the image stream processing algorithm may improve the visibility and reduce or eliminate distortion in the image stream provided by a surgical camera. The image stream processing algorithm may reduce or remove fog, smoke, contaminants, or other obscurities present in the image stream. The types of image stream processing algorithms employed by the image stream processing system 108 may include, for example, a histogram equalization algorithm to improve image contrast, an algorithm including a convolution kernel that improves image clarity, and a color isolation algorithm. The image stream processing system 108 may apply image stream processing algorithms alone or in combination.

The surgical camera 110 may be one usable during a surgical procedure, such an endoscope or laparoscope. The surgical camera 110 may be a camera system comprising a control unit and flexible light source suitable for use in a surgical procedure.

Those skilled in the art will appreciate that the environment in which a medical software tools platform system is utilized may vary between embodiments.

Figure 2:
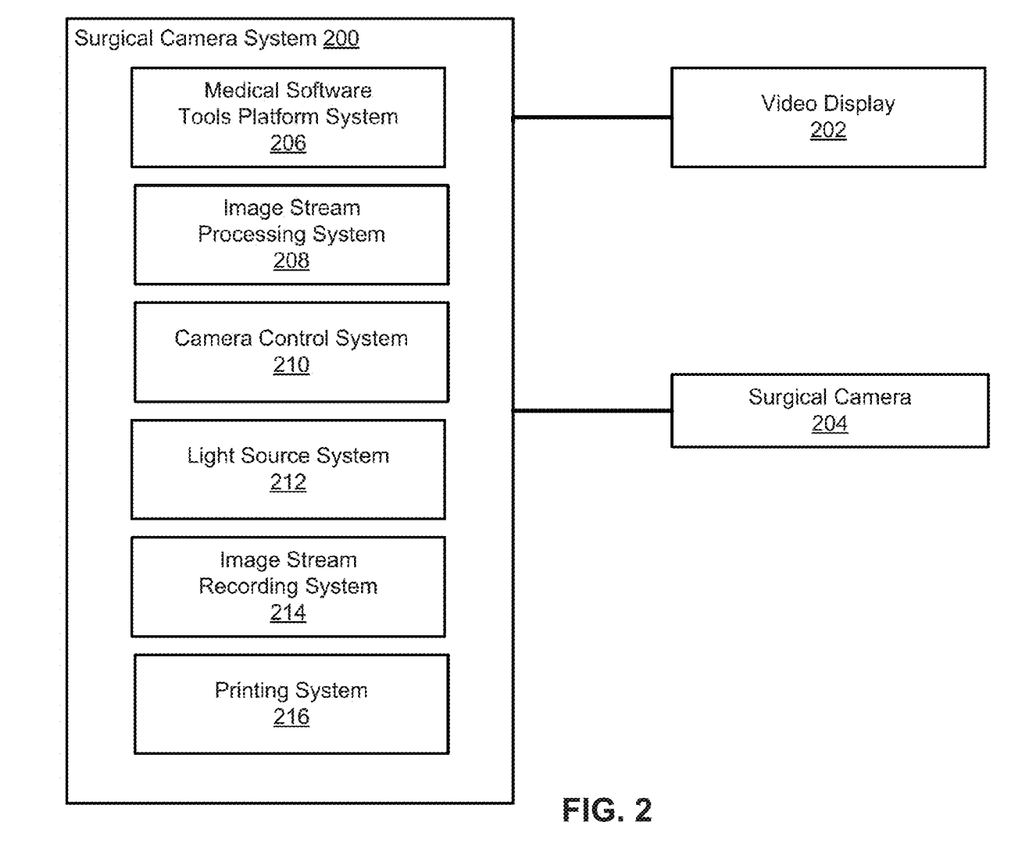
FIG. 2 is a block diagram illustrating an example surgical camera system in accordance with some embodiments of the technology described herein.

FIG. 2 is a block diagram illustrating an example surgical camera system 200 in accordance with some embodiments of the technology described herein. In FIG. 2, the surgical camera system 200 coupled to a video display 202 and coupled to a surgical camera 204, such as an endoscope or laparoscope. It will be appreciated that for some embodiments, the surgical camera 204 may be substituted by another medical device that generates an image stream, such as a medical ultrasound device.

As shown, the surgical camera system 200 includes a medical software tools platform 206, which may be similar to the medical software tools platform system 106 or others described herein. The surgical camera system 200 includes an image stream processing system 208, which may be similar in functionality to the image stream processing system 108. The surgical camera system 200 also includes a camera control system 210 configured to control operation of the surgical camera 204. Depending on the embodiment, the image stream processing system 208 may receive image streams (e.g., video image data) acquired by the surgical camera 204 and processed by the camera control system 210. The surgical camera 204 may include a rigid scope of the type that commonly used for laparoscopy or arthroscopy. The surgical camera 204 may employ charge-coupled devices (CCDs) for acquiring color video image data (e.g., of internal features of the body) through a system of lenses.

The surgical camera 204 may be coupled to the surgical camera system 200 by way of a flexible transmission line. The image stream provided by the surgical camera 204 may comprise video data in analog (e.g., NTSC) or digital (e.g., IEEE 1394) format.

The surgical camera system 200 includes a light source system 212 configured to provide light to the surgical camera 204 as it is utilized during a surgical procedure. The light source system 212 may include a flexible light conduit, such a fiber optic cable, capable of delivering light to locations being observed by the surgical camera 204, which includes locations internal to the surgical patient.

The surgical camera system 200 includes an image stream recording system 214 configured to receive and store a recording of an image stream received, processed, or presented through the surgical camera system 200 (e.g., the video display 202). Depending on the embodiment, the image stream recording system 214 may be analog (e.g., VCR) or a digital recorder.

The surgical camera system 200 includes a printing system 216 configured to generate hard copies of static images captured from an image stream received, processed, or presented through the surgical camera system 200 (e.g., the video display 202). For example, the printing system 216 may generate a hard copy of a static image of an image stream as received from the surgical camera 204, as processed by the image stream processing system 208, as stored by the image stream recording system 214, or as presented in the video display 202 (e.g., with the user interface overlay showing).

Figure 3:
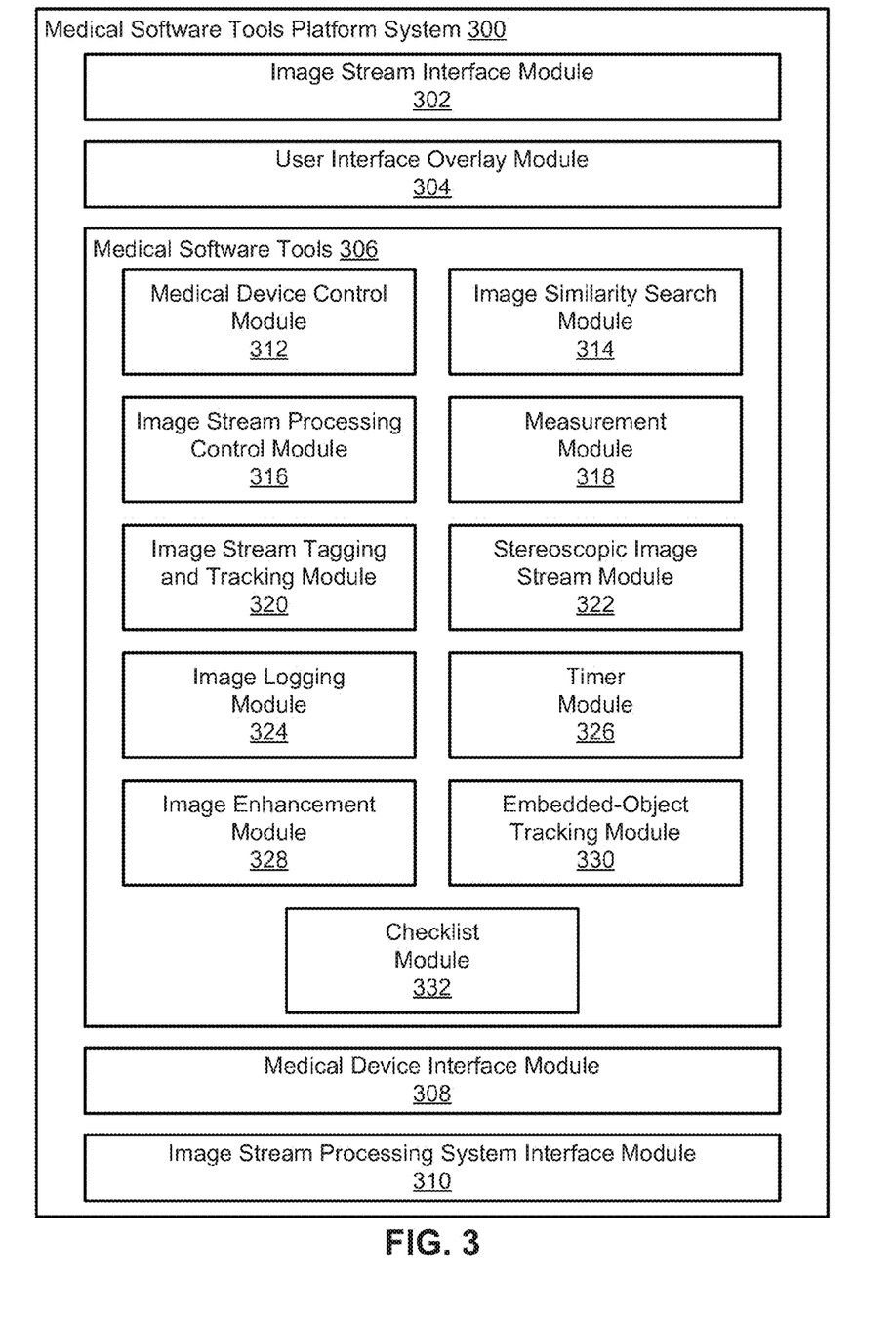
FIG. 3 is a block diagram illustrating an example medical software tools platform system in accordance with some embodiments of the technology described herein.

FIG. 3 is a block diagram illustrating an example medical software tools platform system 300 in accordance with some embodiments of the technology described herein. According to some embodiments, the medical software tools platform system 300 is similar to functionality to the medical software tools platform system 106. In FIG. 3, the medical software tools platform system 300 includes an image stream interface module 302, a user interface overlay module 304, medical software tools 306, a medical device interface module 308, and an image stream processing system interface module 310. In various embodiments, the medical software tools platform system 300 may be integrated, in whole or in part, into a video display or an image stream processing system utilized in an operating room.

The image stream interface module 302 may receive an image stream acquired by a surgical camera or the like. Depending on the embodiment, the image stream may be received directly from the surgical camera, or may be provided by way of one or more components, such as an image stream processing system. The image stream received from the image stream interface module 302 may vary in resolution, frame rate, format, and protocol according to the surgical camera or the image stream processing system providing the image stream.

The user interface overlay module 304 may provide a user interface to the medical software tools platform system 300, which may include one or more graphical user interface (GUI) elements presented over the image stream received through the image stream interface module 302. For some embodiments, the user interface comprises a bottom toolbar configured to be presented over the image stream, and configured to provide access to various medical software tools available through the medical software tools platform system 300.

The medical software tools 306 may include one or more medical software tools, such as medically-oriented applications or widgets, which can be utilized with respect to the image stream being received through the image stream interface module 302. In FIG. 3, the medical software tools 306 includes a medical device control module 312, an image similarity search module 314, an image stream processing control module 316, a measurement module 318, an image stream tagging and tracking module 320, a stereoscopic image stream module 322, an image logging module 324, a timer module 326, an image enhancement 328, an embedded-object tracking module 330, and a checklist module 332.

The medical device control module 312 may facilitate control of one or more various medical devices utilized in an operating room. In particular, the medical device control module 312 may control operation of a medical device or configuring settings of the medical device. Medical devices controllable by way of the medical device control module 312 may include those that are network-enabled using a standard network interface.

The image similarity search module 314 may facilitate identification or search of a texture, shape, structure, or size in content of an image stream based on selected area of the image stream or a reference image. The image similarity search module 314 may include adjustable sensitivity settings for the identification or search operations. The reference image used for the identification or search operation may be one obtained from a patient's medical record, or one previously captured from the image stream from the surgical camera. During identification operations, the image similarity search module 314 may augment the image stream with visual indicators (e.g., hatching, call outs, lead lines, arrows, highlighting, or labels) to indicate similar texture, shape, structure, or size.

The image stream processing control module 316 may facilitate control of an image stream processing system utilized in an operating room to process an image stream acquired by a surgical camera or the like. Depending on the embodiment, the image stream processing control module 316 may determine which image stream processing algorithms are applied to the image stream before it is presented on a video display.

The measurement module 318 may facilitate measurement of one or more anatomical structures or tissue presented in the content of an image stream received through the image stream interface module 302. Depending on the embodiment, measurement module 318 may enable a user (e.g., surgeon) to select a region in the image stream and determine a measurement based on the selected region. The measurement may include linear measurements (e.g., width, height, length) and volumetric measurements of an anatomical structure or tissue delineated by the selected region.

The image stream tagging and tracking module 320 may facilitate placement of one or more visual tags with respect to an anatomical structure or tissue presented in an image stream received through the image stream interface module 302. Once placed, the visual tag may be presented over the anatomical structure or tissue through the user interface provided by the user interface overlay module 304. The image stream tagging and tracking module 320 may also facilitate tag tracking such that the visual tags continue to maintain their position with respect to the anatomical structure or tissue (or some other specimen) when positioning between the surgical camera and the anatomical structure or tissue changes. In this way, the visual tags can be "sticky" with respect to the anatomical structure or tissue and correctly indicate their original placement with respect to the anatomical structure or tissue. Where the anatomical structure or tissue goes out of view (e.g., goes off screen), the image stream tagging and tracking module 320 may restore visual tag positioning when the anatomical structure or tissue returns into view. Depending on the embodiment, a visual tag may be associated with textual, audio, or video commentary, or associated with a timer (e.g., clock, countdown timer, stop-watch, alarm) added through a component of the medical software tools platform system 300 (e.g., the timer module 326). Depending on the embodiment, the visual tags may comprise hatching, call outs, lead lines, arrows, highlighting, or labels. In some instances, a tag can serve as a bookmark to a location of interest for a medical procedure. For example, as a bookmark a tag may assist a user (e.g., a surgeon) in visually revisiting locations of events that have occurred during a medical procedure, such as the location of a tissue biopsy or the insertion location of an object embedded in a patient's body (e.g., a sponge, clamp, or staple).

The stereoscopic image stream module 322 may facilitate conversion of two-dimensional content in an image stream to stereoscopic three-dimension content. Through the conversion process, the stereoscopic image stream module 322 may enhance two-dimensional imagery of anatomical structures or tissue in the image stream to stereoscopic three-dimensional imagery of anatomical structures or tissue. Depending on the embodiment, stereoscopic image stream module 322 may convert some or all (e.g., selected portions) of the image stream to stereoscopic three-dimensional content. Additionally, the medical software tools 306 may include an image stream module that utilizes non-stereoscopic methodology in generating three-dimensional content from two-dimensional content.

The image logging module 324 may facilitate recording operations with respect to an image stream. According to some embodiments, the image logging module 324 enables recording of the image stream with a voice-over or a bookmark, or capturing of frames from an image stream (e.g., drag-and-drop a frame from the image stream to a window). Some or all of the functionality of the image logging module 324 may be facilitated through an image stream recording system or an image stream processing system.

The timer module 326 may facilitate the addition of one or more countdown timers, clocks, stop-watches, alarms, or the like, that can be added and displayed over the image stream through the user interface provided by the user interface overlay module 304. For example, the timer module 326 may allow a user (e.g., surgeon) to add a countdown timer in association with a surgical step (e.g., clamping an artery). For example, a countdown timer may be associated with a specific blood vessel that must be temporarily clamped during surgery but must be opened within a small window of time. A user may be able to select from a list of pre-defined countdown timers, which may have been pre-defined by the user. A clock when added may be used as a time bookmark during surgical procedures.

The image enhancement 328 may facilitate improving the resolution of an image stream using information from several different frames to create new, higher resolution frames. The image enhancement 328 may further facilitate zooming to enlarge selected regions of the image stream. For some embodiments, the image enhancement 328 may utilize an image stream processing system in implementing some or all the image enhancements it applies.

The embedded-object tracking module 330 may enable a user (e.g., surgeon) to track objects embedded in a patient's body (hereafter, "embedded objects") during a medical procedure, such a sponges, clamps, and the like. For example, the embedded-object tracking module 330 may enable tracking of embedded objects by allowing a user to maintain a count of embedded objects used during a medical procedure. According to some embodiments, the embedded-object tracking module 330 maintains the count by adding to the count when objects are embedded in a patient's body, and subtracting from the count when embedded objects are removed from within the patient's body. The count may be maintained manually by way of user input (e.g., by a surgeon's input to a touch screen display), or automatically by way of a process (e.g., imaging process) configured to automatically detect the addition or removal of embedded objects. For some embodiments, the count of embedded objects is maintained according to categories, such as object type (e.g., a separate count for sponges, and a separate count for clamps) or association to a procedural step.

The embedded-object tracking module 330 may also track embedded objects by maintaining a listing of the objects embedded into a patient's body during a medical procedure. For example, the embedded-object tracking module 330 may maintain the list of embedded objects by a user indicating, or a process automatically detecting, when a particular embedded object has been added to a patient's body or when the particular embedded object has been removed from the patient's body. In addition, the listing of objects may include the count of embedded object as described herein.

The embedded-object tracking module 330 may further track embedded objects by remembering the location of embedded objects in a patient's body. Once remembered, the embedded-object tracking module 330 may include visual indicators with respect to such embedded objects when they appear on a video display, such as highlighting or indicator lines.

Through use of the embedded-object tracking module 330, a user (e.g., surgeon) can account for various embedded objects used during a medical procedure or a step thereof. The embedded-object tracking module 330 can also help ensure that embedded objects have not been inadvertently left within a patient's body at the conclusion of a medical procedure or a step thereof, such as before a patient is surgically closed-up.

The checklist module 332 may enable a user (e.g., surgeon) to maintain a checklist in connection with a medical procedure. For example, the checklist module 332 may provide a list of checklist items for a medical procedure. Each checklist item may indicate whether a step of the medical procedure has been completed or has yet to be completed. The checklist module 332 may allow a user to present the checklist in different ways. For instance, the checklist items may be organized and presented according to their procedural order, their importance, their relation to a patient's anatomy, their category, or their assigned individual (e.g., checklist item is the nurse's responsibility versus the surgeon's responsibility). In another example, the checklist items may be presented in using a different visual structures, such as a tree structure or a scrolling list.

The medical device interface module 308 may facilitate communication between the medical software tools platform system 300, one or more of the medical software tools 306, and one or more various medical devices utilized in an operating room. For instance, the medical device interface module 308 may enable the medical device control module 312 to control one or more medical devices utilized during a surgical procedure. Accordingly, the medical device interface module 308 may transmit control data to a medical device, or receive information collected by a medical device. The medical device interface module 308 may include various data interfaces, including wired or wireless network interfaces and serial communication interfaces.

The image stream processing system interface module 310 may facilitate communication between the medical software tools platform system 300 and an image stream processing system utilized to process an image stream acquired by a surgical camera or the like. Through the communication, the image stream processing system interface module 310 may transmit control data to an image stream processing system, or receive an image stream from a surgical camera as processed by the image stream processing system. The image stream processing system interface module 310 may include various data interfaces, including wired or wireless network interfaces and serial communication interfaces.

Figure 4:
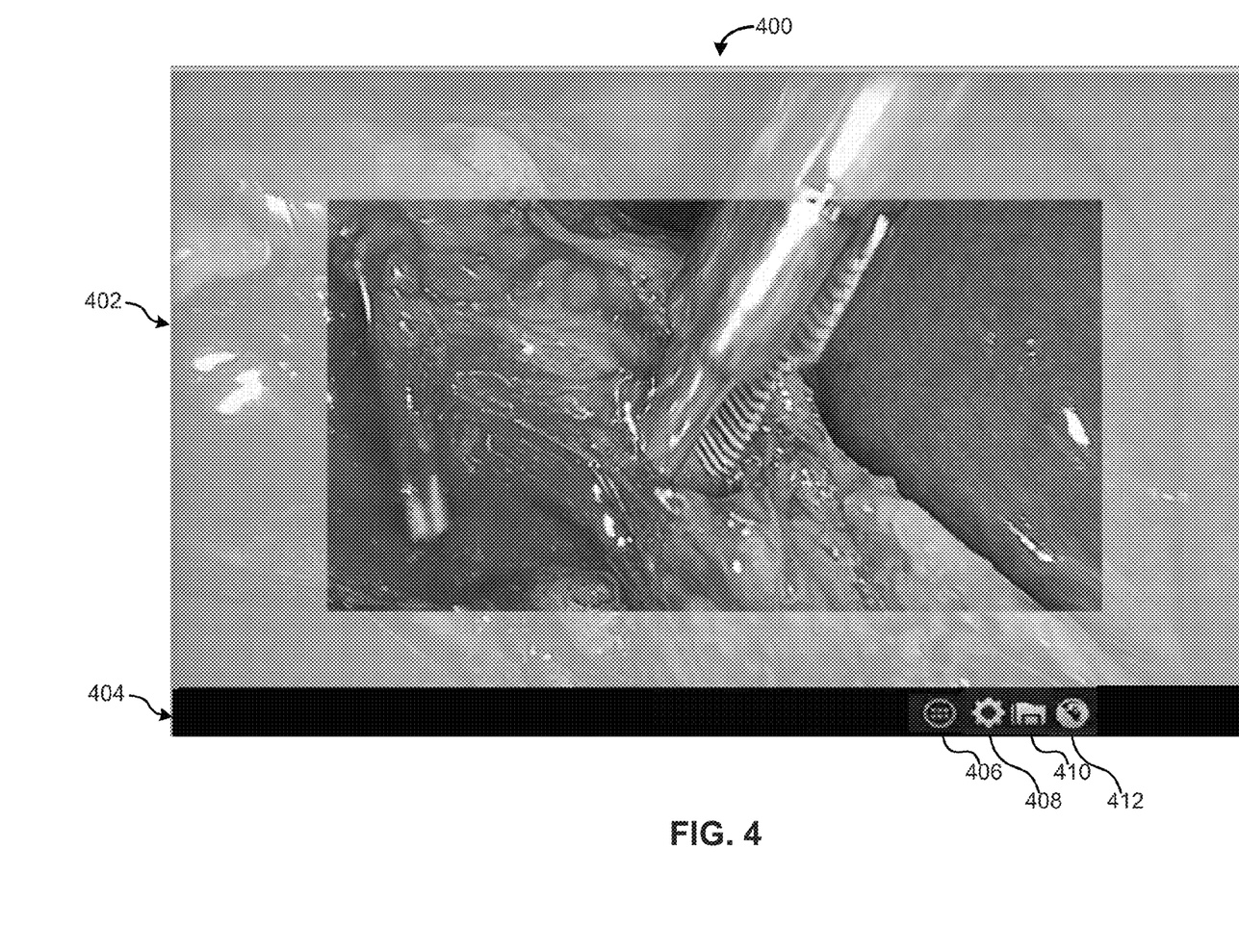
FIG. 4 a screenshot illustrating an example user interface overlay of a medical software tools platform system over an image stream in accordance with some embodiments of the technology disclosed herein.

FIG. 4 a screenshot 400 illustrating an example user interface overlay 404 of a medical software tools platform system over an image stream 402 in accordance with some embodiments of the technology disclosed herein. The screenshot 400 may be one presented on a video display commonly used in an operating room, such as a surgical display used with an endoscope. As described herein, a surgical camera, medical ultrasound device, or the like may provide the image stream 402. Additionally, the image stream 402 may be one processed by an image stream processing system before being presented on a video display.

In FIG. 4, the user interface overlay 404 includes: a) an icon 406 to access a menu of medical software tools provided by the medical software tools platform; b) an icon 408 to access settings for the medical software tools platform system associated with the user interface overlay 404; c) an icon 410 to access data accessible by the medical software tools platform system, such as data provided by a medical records system or other medical device utilized in the operating room; and d) an icon 412 to access web browser with access to the Internet, intranet (e.g., hospital intranet), or extranet. It will be understood that in various embodiments, the look of the user interface overlay may differ from what is depicted in FIG. 4. For some embodiments, additional graphical user interface elements may be presented over the image stream based on one or more operations performed by the medical software tools platform or it associated medical software tools.

Figure 5:
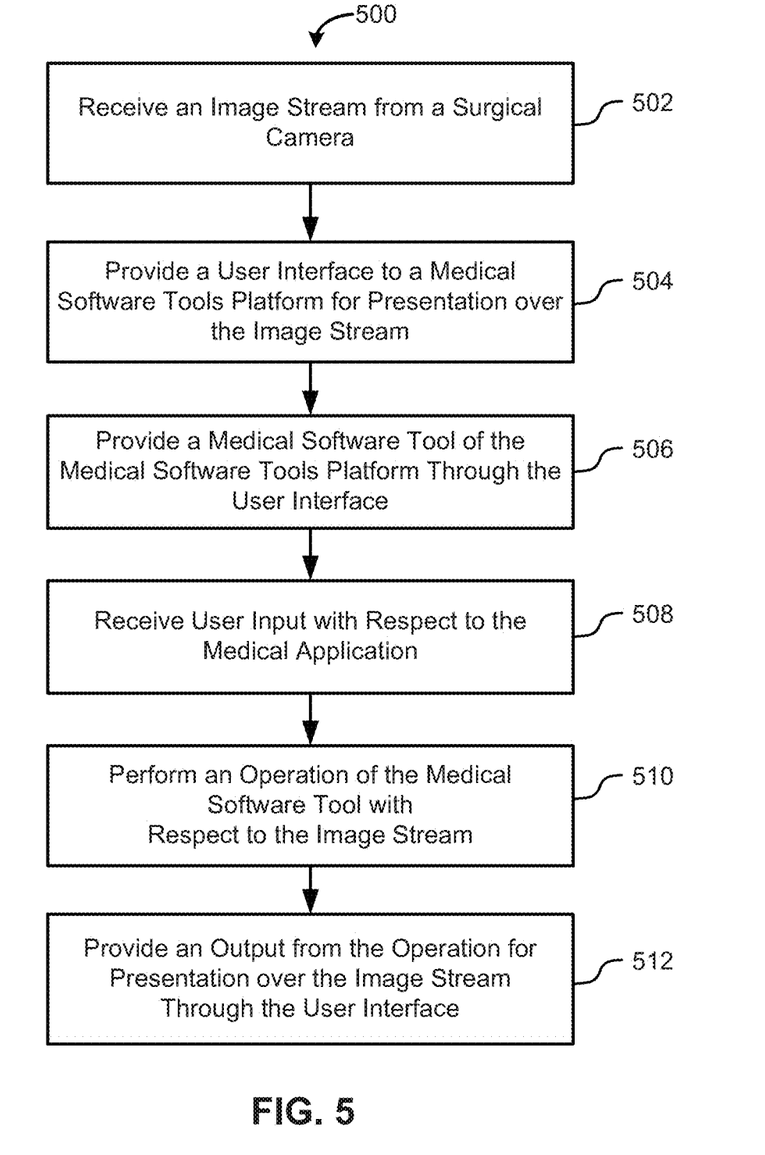
FIG. 5 a flowchart illustrating an example method for a medical software tools platform in accordance with some embodiments of the technology disclosed herein.

FIG. 5 a flowchart illustrating an example method 500 for a medical software tools platform in accordance with some embodiments of the technology disclosed herein. According to some embodiments, the method 500 may be one performed by the medical software tools platform system 106 as the system 106 is providing a user interface overlay for presentation over an image stream being presented on the video display 102.

As shown in FIG. 5, the method 500 may begin at operation 502 with an image stream being received from a surgical camera or the like. For example, an image stream may be received from the surgical camera 110, or from the image stream processing system 108 that processes the image stream from the surgical camera 110.

At operation 504, a user interface to a medical software tools platform is provided for presentation over the image stream received at operation 502. For example, the user interface may be provided by the user interface overlay module 304. Providing the user interface may comprise generating, or presenting, the user interface to the medical software tools platform.

At operation 506, a medical software tool of the medical software tools platform is provided through the user interface provided at operation 504. For example, the medical software tools may be one or more of the medical software tools 306. Providing the medical software tool may comprise generating, or presenting, a user interface of the medical software tool through the user interface.

At operation 508, user input is received with respect to the medical software tool provided at operation 506. For example, user input may be received as voice commands, through a touch-enabled video display, or through such human input devices as keyboards or mice. The user input may be received through the user interface provided by the user interface overlay module 304.

At operation 510, an operation of the medical software tool is performed with respect to the image stream received at operation 502. For example, operations performed by the medical software tools 306 may include, without limitation, image stream enhancement, management of windows for window-based functions, timers (e.g., clocks, countdown timers, and time-based alarms), tagging and tag tracking, image stream logging, performing measurements, two-dimensional to three-dimensional content conversion, and similarity searches.

Figure 6:
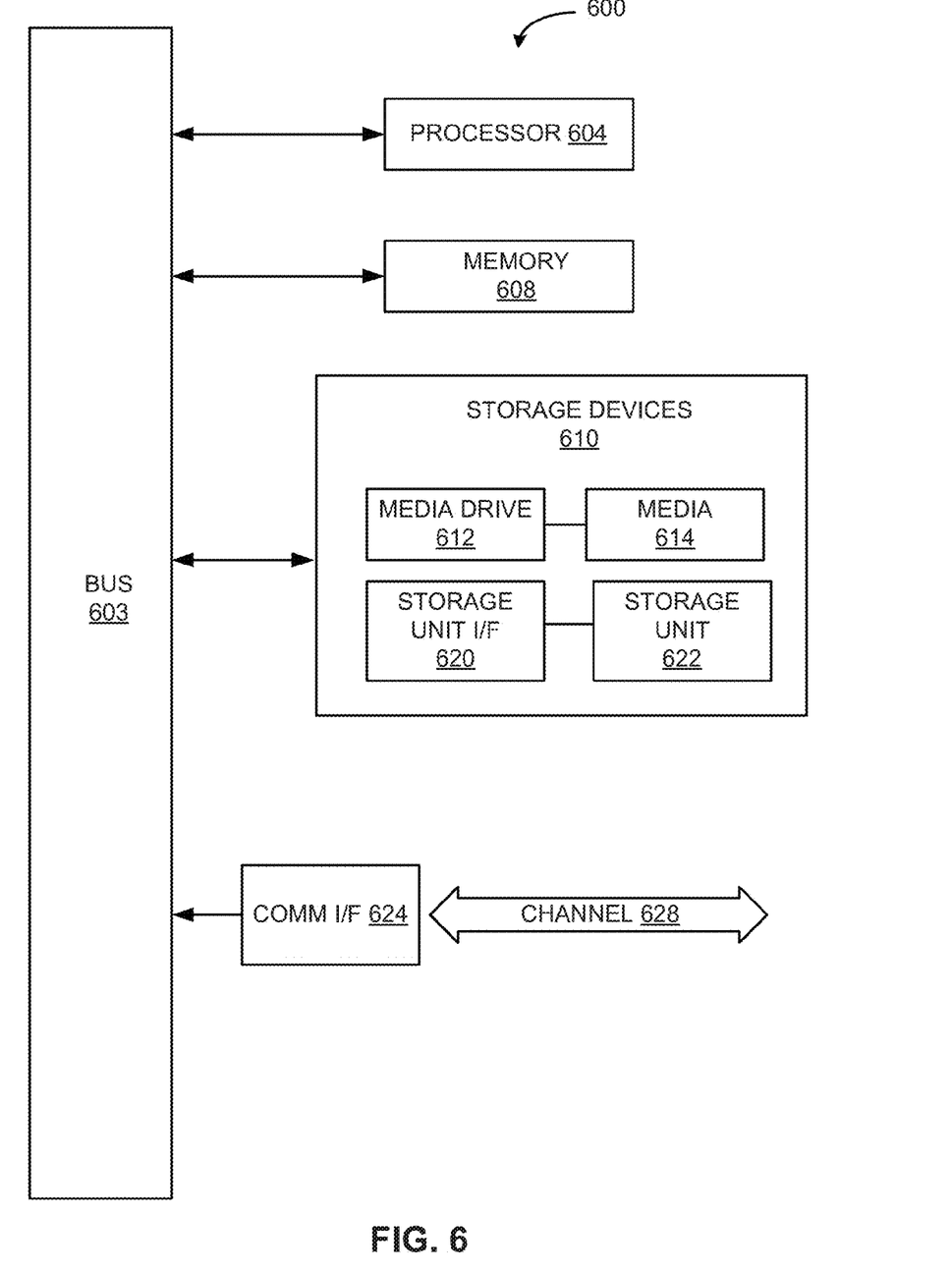
FIG. 6 illustrates an example computing module that may be used in implementing various features of embodiments of the disclosed technology.

At operation 512, output from the operation performed at operation 510 is provided for presentation through the user interface provided at operation 504. For example, output from operations may include, without limitation, enhanced image stream, placement of windows, presentation of timers, presentation of visual tags, presentation of measurements, three-dimensional content (e.g., stereoscopic three-dimensional imagery of anatomical structures), and identification of similarities in an image stream.

Where components or modules of the technology are implemented in whole or in part using software, in one embodiment, these software elements can be implemented to operate with a computing or processing module capable of carrying out the functionality described with respect thereto. One such example computing module is shown in FIG. 6. Various embodiments are described in terms of this example—computing module 600. After reading this description, it will become apparent to a person skilled in the relevant art how to implement the technology using other computing modules or architectures.

Referring now to FIG. 6, computing module 600 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 600 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 600 might include, for example, one or more processors, controllers, control modules, or other processing devices, such as a processor 604. Processor 604 might be implemented using a general-purpose or special-purpose processing engine such as, for example, a microprocessor, controller, or other control logic. In the illustrated example, processor 604 is connected to a bus 603, although any communication medium can be used to facilitate interaction with other components of computing module 600 or to communicate externally.

Computing module 600 might also include one or more memory modules, simply referred to herein as main memory 608. For example, preferably random access memory (RAM) or other dynamic memory might be used for storing information and instructions to be executed by processor 604. Main memory 608 might also be used for storing temporary variables or other intermediate information during execution of instructions to be executed by processor 604. Computing module 600 might likewise include a read only memory ("ROM") or other static storage device coupled to bus 603 for storing static information and instructions for processor 604.

The computing module 600 might also include one or more various forms of information storage mechanism 610, which might include, for example, a media drive 612 and a storage unit interface 620. The media drive 612 might include a drive or other mechanism to support fixed or removable storage media 614. For example, a hard disk drive, a floppy disk drive, a magnetic tape drive, an optical disk drive, a CD or DVD drive (R or RW), or other removable or fixed media drive might be provided. Accordingly, storage media 614 might include, for example, a hard disk, a floppy disk, magnetic tape, cartridge, optical disk, a CD or DVD, or other fixed or removable medium that is read by, written to, or accessed by media drive 612. As these examples illustrate, the storage media 614 can include a computer usable storage medium having stored therein computer software or data.

In alternative embodiments, information storage mechanism 610 might include other similar instrumentalities for allowing computer programs or other instructions or data to be loaded into computing module 600. Such instrumentalities might include, for example, a fixed or removable storage unit 622 and an interface 620. Examples of such storage units 622 and interfaces 620 can include a program cartridge and cartridge interface, a removable memory (for example, a flash memory or other removable memory module) and memory slot, a PCMCIA slot and card, and other fixed or removable storage units 622 and interfaces 620 that allow software and data to be transferred from the storage unit 622 to computing module 600.

Computing module 600 might also include a communications interface 624. Communications interface 624 might be used to allow software and data to be transferred between computing module 600 and external devices. Examples of communications interface 624 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 624 might typically be carried on signals, which can be electronic, electromagnetic (which includes optical) or other signals capable of being exchanged by a given communications interface 624. These signals might be provided to communications interface 624 via a channel 628. This channel 628 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 608, storage unit 622, media 614, and channel 628. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 600 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A system for medical software tools, comprising:
an image stream interface module configured to receive an image stream from a surgical camera;
a user interface overlay module configured to provide a user interface overlay adapted for presentation over the image stream;
a medical software tools module configured to provide a medical software tool through the user interface, the medical software tool being configured to perform an operation with respect to the image stream and provide an output adapted to be presented over the image stream;
an image stream processing module for facilitating control of an image stream utilized in an operating room to process an image stream acquired from an optical surgical sensor;
a measurement module for facilitating measurement of one or more anatomical tissue structures presented by said image steam processing module; and
an image stream tagging module for facilitating placement of one or more visual tags corresponding with said one or more tissue structures presented by said image processing module for real time documentation of said one or more anatomical tissue structures located within a patient's body, wherein said image stream is either converted from a two dimensional to a three dimensional image to facilitate surgical procedures performed within a patient's body or otherwise enhanced via image resolution modulation.

2. The system of claim 1, wherein the user interface overlay module is further configured to present the output over the image stream in combination with image enhancement in order to facilitate surgical procedures located within a patient's body.

3. The system of claim 1, wherein the surgical camera is an endoscope or a laparoscope adapted to include image enhancement by either enlarging various images or increasing resolution of various images for assisting a surgeon for conducting surgical procedures within said body of a patient.

4. The system of claim 1, wherein the image stream interface module is further configured to receive the image stream from the surgical camera through an image stream processing system incorporating image enhancement or conversion from a two dimensional image to a three dimensional image.

5. The system of claim 1, further comprising a medical device interface module configured to exchange data between a medical device and the medical software tool for facilitating surgical procedures within a body of a patient.

6. The system of claim 1, further comprising an image stream processing system interface module configured to exchange data between an image stream processing system and the medical software tool, the medical software tool being configured to modify a setting of the image stream processing system, and wherein said exchanged data includes both standard images and enhanced images.

7. The system of claim 6, wherein the setting includes enabling or disabling application of an image stream processing algorithm to the image stream for enhancing said image stream by either modulating resolution or creating a three dimensional image stream.

8. The system of claim 1, wherein the operation comprises disposing a visual tag over the image stream in association with an anatomical structure or tissue within a body of a patient presented in the image stream, and the output comprises the visual tag.

9. The system of claim 8, wherein the operation further comprises associating a timer with respect to the visual tag for assisting a surgeon performing a procedure within a body of a patient and wherein said timer measures time corresponding to said procedure for assisting a surgeon for conducting a surgical procedure with said body of a patient.

10. The system of claim 1, wherein the operation comprises measuring an anatomical structure or tissue within a body of a patient presented in the image stream, and the output comprises a resulting measurement corresponding with said anatomical structure or tissue.

11. The system of claim 1, wherein the image stream comprises two-dimensional content, the operation comprises converting at least some of the two-dimensional content into three-dimensional content, and the output comprises the three-dimensional content.

12. The system of claim 1, wherein the operation comprises associating content in the image stream with a timer, and the output comprises a visual representation of the timer.

13. The system of claim 1, wherein the operation comprises identifying content in the image stream similar to reference content, and the output comprises a visual indication of the identified content.

14. A method for medical software tools, comprising:
a computer system receiving an image stream from a surgical camera;
the computer system providing a user interface overlay adapted for presentation over the image stream;
the computer system providing a medical software tool through the user interface;
the computer system performing an operation of the medical software tool with respect to the image stream;
the computer system providing an output of the operation for presentation over the image stream, wherein said image stream is utilized within an operating room; a measurement module for facilitating measurement of one or more anatomical tissue structures presented by said image stream processing module; and
an image stream tagging module for facilitating placement of one or more visual tags corresponding with said one or more tissue structures presented by said image processing module for real time documentation of said one or more anatomical tissue structures located within a patient's body, wherein said image stream is either converted from a two dimensional to a three dimensional image to facilitate surgical procedures within a patient's body or otherwise enhanced via image resolution modulation.

15. The method of claim 14, further comprising the computer system presenting the output over the image stream in order to facilitate surgical procedures located within a patient's body.

16. The method of claim 14, wherein the surgical camera is an endoscope or a laparoscope adapted to correspond with image enhancement by either enlarging various images or increasing resolution of various images.

17. The method of claim 14, wherein the computer system receives the image stream from the surgical camera through an image stream processing system incorporating image enhancement.

18. The method of claim 14, wherein the medical software tool is configured to modify a setting of the image stream processing system including a setting for image resolution modulation.

19. The method of claim 18, wherein the setting includes enabling or disabling application of an image stream processing algorithm to the image stream, wherein said setting further includes the ability to provide three dimensional images.

20. The method of claim 14, wherein the operation comprises disposing a visual tag over the image stream in association with an anatomical structure or tissue presented in the image stream, and the output comprises the visual tag, wherein said visual tag corresponds to a selected anatomical structure or tissue located within the body of a patient and wherein said image stream may be enhanced either by resolution modulation or a three dimensional output.

21. The method of claim 20, wherein the operation further comprises associating a timer with respect to the visual tag, wherein said timer provides assistance for a surgeon performing a procedure within a body of a patient and wherein said timer measures time corresponding to said procedure.

22. The method of claim 14, wherein the operation comprises measuring an anatomical structure or a tissue presented in the image stream, and the output comprises a resulting measurement, wherein said measurement corresponds with a physical property located within the body of a patient and wherein said image stream is enhanced by resolution modulation or output as a three dimensional image.

23. The method of claim 14, wherein the image stream comprises two-dimensional content, the operation comprises converting at least some of the two-dimensional content into three-dimensional content, and the output comprises the three-dimensional content.

24. The method of claim 14, wherein the operation comprises associating content in the image stream with a timer, and the output comprises a visual representation of the timer.

25. The method of claim 14, wherein the operation comprises identifying content in the image stream similar to reference content, and the output comprises a visual indication of the identified content.

* * * * *